United States Patent [19]

Young

[11] 4,365,083

[45] Dec. 21, 1982

[54] PREPARATION OF ALKYL CARBOXYLATES

[75] Inventor: Lewis B. Young, Skillman, N.J.

[73] Assignee: Mobil Oil Corporation, New York, N.Y.

[21] Appl. No.: 217,979

[22] Filed: Dec. 19, 1980

[51] Int. Cl.$^3$ ............................................. C07C 67/04
[52] U.S. Cl. ............................ 560/247; 260/410.9 R; 560/103; 560/106; 560/226; 560/227; 560/241
[58] Field of Search ............... 560/247, 241, 103, 226, 560/106; 260/410.9 R

[56] References Cited

U.S. PATENT DOCUMENTS

| | | | |
|---|---|---|---|
| 3,014,066 | 12/1961 | Kerr | 560/247 |
| 3,085,108 | 4/1963 | Stepanek | 560/247 |
| 3,096,365 | 7/1963 | Heisler | 560/247 |
| 3,492,341 | 1/1970 | Trevillyan | 560/247 |

*Primary Examiner*—Michael L. Shippen
*Attorney, Agent, or Firm*—Charles A. Huggett; Michael G. Gilman; George W. Allen

[57] ABSTRACT

A method for preparation of alkyl carboxylate compounds, and especially methylalkyl carboxylate compounds, by reaction of an olefin and a carboxylic acid compound in the presence of a mordenite catalyst.

6 Claims, No Drawings

PREPARATION OF ALKYL CARBOXYLATES

BACKGROUND OF THE INVENTION

1. Field of the Invention

This invention is concerned with a novel method for preparation of alkylcarboxylates, and particularly α-methylalkyl carboxylates, by reaction of carboxylic acids with olefinic compounds in the presence of a particular type of crystalline zeolite catalyst.

2. Description of the Prior Art

The addition of carboxylic acids to olefins to make esters is known. The chemical literature describes the use of Lewis acid catalysts, such as $BF_3$, to promote the reaction. However, particularly in the case of internal olefins, the reaction will result in addition of the carboxylic acid to both ends of the double bond, thereby giving rise to a mixture of carboxylate products. Mineral acids (e.g., $H_2SO_4$) are also reported to catalyze the reaction, but the result is much the same, i.e., non-selective addition of the carboxylic acid to either side of the carbon-carbon double bond.

In the past, the only known reaction route to produce α-methylalkyl carboxylates directly has required the utilization of expensive alpha-olefins. Reaction with internal or mixed olefins has necessitated physical separation of the isomeric variants by other means, such as distillation, in order to isolate a product which is rich in the α-methylalkyl carboxylate.

Alkyl esters of carboxylic acids are useful as solvents, plasticizers and chemical intermediates. α-Methylalkyl carboxylates are particularly useful for making secondary alcohols with hydroxyl attachment at the 2-carbon. By utilization of the herein disclosed method, products normally derived from pure α-olefins can now be prepared from less expensive linear olefin mixtures.

SUMMARY OF THE INVENTION

It has now been discovered that certain zeolite materials may be utilized to promote reaction between olefins and carboxylic acids to produce alkyl carboxylates. In a particularly preferred embodiment, α-methylalkyl carboxylates are prepared as the major product from the reaction of carboxylic acids and internal linear olefins, olefin mixtures or α-olefins. Specifically, the α-methylalkyl carboxylates contemplated herein are those described by the formula:

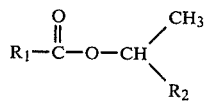

wherein:
$R_1$ = alkyl, aryl, haloalkyl or hydrogen
$R_2$ = $C_1$-$C_{20}$ alkyl, heteroalkyl or cycloalkyl The method comprises reacting a carboxylic acid having the formula

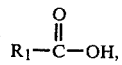

$R_1$ being described above, with an olefin having from 3 to about 20 carbon atoms. Substantially any linear, slightly branched, cyclic or heteroatom-substituted olefin may be employed, regardless of the position of the carbon-carbon double bond. However, linear olefins are preferred.

A wide range of temperature and pressure conditions are found to be conducive to the reaction, which may be successfully carried out at 25° C. to 600° C. and $10^4$ Pa to $10^7$ Pa (0.1 to 100 atmospheres) pressure. Temperatures of between 75° C. and 400° c. are preferred, as are pressures of $10^5$ Pa to $40 \times 10^5$ Pa (1 to 40 atmospheres). The reaction may be usefully carried out in either the liquid or vapor phase, although it may be found preferable to employ liquid phase reaction.

The zeolite material employed to promote the novel, selective addition reaction of this invention is zeolite mordenite. The mordenite may be synthetically prepared or naturally occurring. De-aluminized mordenites, i.e. those subjected to acid treatment to increase the silica to alumina mole ratio to a relatively high level, are preferred.

DESCRIPTION OF SPECIFIC EMBODIMENTS

A one-step process has now been found for the manufacture of alkyl carboxylates from carboxylic acids and olefins, with especially desirable selectivity to α-methylalkyl carboxylates. By utilization of the particular zeolite catalyst described hereinafter, it now becomes possible to react carboxylic acids with olefins having the carbon-carbon double bond in substantially any position in the molecule and produce an adduct wherein the carboxylate has attached principally at the #2 carbon of the olefin molecule. This is in striking contrast to the reaction product resulting from utilization of Lewis acid and mineral acid catalysts wherein the carboxylate would attach at the carbons on either side of the double bond and, unless the site of the unsaturation included the #2 carbon atom, the resultant yield of α-methylalkyl carboxylates would comprise no more than a minor byproduct.

The carboxylic acids useful in the process of the present invention are preferably alkyl carboxylic acids having from 1 to about 10 carbon atoms therein. Included within this group are, for example, formic acid, acetic acid, propionic acid, butyric acid and hexanoic acid. Slightly branched alkyl carboxylic acids are also useful, such as, for instance, isobutyric acid. Haloalkyl carboxylic acids, such as chloroacetic acid, fluoroacetic acid and trifluoroacetic acid may be employed. Also, aryl carboxylic acids will be found desirable in some instances, including benzoic acid, para-toluic acid and para-chlorobenzoic acid.

Olefins suitable for manufacture of α-methylalkyl carboxylates as described herein are not limited to α-olefins. Rather, it has been found that substantially any olefinic hydrocarbons may be employed without regard to the location of the site of unsaturation. Mixed isomers of a given olefin are particularly desirable due to their ready availability and relatively low cost. Linear $C_3$-$C_{20}$ olefins are especially preferred, but slightly branched olefins may also be employed. Some non-limiting examples include propylene, butene, octene, dodecene, hexadecene and 1-methylnonene.

Addition of carboxylic acids to cyclic olefins may also be carried out by the present procedure. Such cyclic olefins would include, for example, cyclohexene, cyclopentene, methylcyclopentene, norbornene, and camphene.

Although hydrocarbon olefinic compounds are preferred, one may in some cases wish to utilize hetero-substituted olefins. Some illustrative examples of useful compounds would include butenyl acetate and chlorooctene.

The zeolite material utilized as the catalyst in the process of this invention is known as mordenite. This zeolite is naturally occurring and, in its natural state, normally has a silica to alumina mole ratio approximately equal to 5-10. However, a large part of the alumina can be removed from the mordenite crystal framework, thereby substantially increasing the silica to alumina mole ratio, by acid extraction or "leaching". This increases the effective pore diameter and thus diffusivity of reactant and product molecules to and from the active sites. Acid extraction, commonly referred to as de-aluminization of the zeolite, is generally accomplished by treatment with strong mineral acids which, in addition to removing $Al_2O_3$, also replace metal cations (e.g. $Na^+$) with hydrogen ions. In the process of the hereindisclosed invention, the utilization of de-aluminized mordenites is preferred.

Mordenite can also be prepared synthetically. One method of synthesis is disclosed by L. B. Sand in U.S. Pat. No. 3,436,174. Another will be found in U.S. Pat. No. 3,574,539, issued to D. Domine and J. Quobex. Both patents are incorporated herein by reference for the purpose of showing synthetic methods of mordenite preparation.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The process of this invention is carried out such that the organic reactants, i.e., the carboxylic acid and the olefinic compound, are brought into contact with the particular type of zeolite material described herein in a suitable reaction zone. The temperature is elevated to a level conducive to the addition reaction. Suitable temperatures are from about 25° C. to about 600° C., but temperatures of between 75° C. and 400° C. are preferred. The reaction zone will preferably be pressurized to approximately $10^5$ Pa to $40 \times 10^5$ Pa (1 to 40 atmospheres) pressure, but pressures falling within the range of $10^4$ Pa to $10^7$ Pa (0.1 to 100 atmospheres) will be found to be utilizable.

The alkylation process described herein may be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

The following examples are provided to illustrate the process of this invention and to aid those in the art in the understanding thereof, but clearly should not be taken as presenting undue limitations thereon:

EXAMPLE 1

A sample of a commercially available mordenite zeolite catalyst (Zeolon 500) was de-aluminized by extraction with 0.5 N HCl to adjust the silica to alumina mole ratio to approximately 85. One-tenth of a gram of the dried, de-aluminized zeolite was ground to a powder and added to 10 ml of a mixture of 1-decene and acetic acid (mole ratio = 1:4). The mixture was heated to reflux and samples were periodically removed and analyzed. As will be seen from the summary provided in TABLE I, the product of the reaction was overwhelmingly the 2-isomer (2-decylacetate) with minor amounts of the 3-, 4- and 5-isomers as byproducts.

TABLE I

| Reaction Of 1-Decene And Acetic Acid | | | |
|---|---|---|---|
| Temperature | 120° C. | 120° C. | 120° C. |
| Reaction Time, hrs. | 1 | 25 | 47 |
| $C_{10}$ Product Distribution | | | |
| $C_{10}H_{20}$ | 65 wt % | 29 wt % | 29 wt % |
| $C_{10}H_{21}OAc$ | 26 wt % | 58 wt % | 58 wt % |
| $(C_{10}H_{20})_2$ | 9 wt % | 13 wt % | 13 wt % |
| $C_{10}H_{21}OAc$ Isomer Distribution | | | |
| 2- | | 80% | 75% |
| 3- | | 19% | 23% |
| 4- | | 0.9% | 1.3% |
| 5- | | 0.2% | 0.3% |

EXAMPLE 2

Using another sample of the same mordenite catalyst, 1-octene and acetic acid (mole ratio = 1:4) were reacted in the manner described in Example 1. The results of the analysis are shown in TABLE II. Again, it is seen that the 2-isomer (2-octylacetate) is selectively produced relative to the higher isomers.

TABLE II

| Reaction Of 1-Octene And Acetic Acid | | | |
|---|---|---|---|
| Temperature | 120° C. | 120° C. | 120° C. |
| Reaction Time, hrs. | 2.5 | 5 | 23 |
| $C_8$ Product Distribution | | | |
| $C_8H_{16}$ | 61.6 wt % | 47.9 wt % | 36.6 wt % |

TABLE II-continued

| Reaction Of 1-Octene And Acetic Acid | | | |
|---|---|---|---|
| C$_8$H$_{17}$OAc | 31.7 wt % | 45.5 wt % | 57.8 wt % |
| (C$_8$H$_{16}$)$_2$ | 6.7 wt % | 6.6 wt % | 5.6 wt % |
| C$_8$H$_{17}$OAc Isomer Distribution | | | |
| 2- | | 93.6% | 91.6% | 85.4% |
| 3- | | 6.4% | 8.4% | 14.0% |
| 4- | | — | — | 0.6% |

EXAMPLE 3

2-Octene and acetic acid (mole ratio=1:2) were reacted in the presence of the mordenite catalyst as described above. The results are summarized in TABLE III.

EXAMPLE 4 (Comparative)

A mixture of 2-octene and acetic acid (mole ratio=1:4) were reacted in the presence of a conventional Lewis Acid catalyst (boron trifluoride etherate). The reaction was carried out on a steam bath at 90° C. and samples were removed and analyzed at 1.2 and 2.7 hours. The results are given in TABLE III.

TABLE III

| Reaction Of 2-Octene And Acetic Acid | | | | | |
|---|---|---|---|---|---|
| | Catalyst | | | | |
| | Mordenite | | | BF$_3$—Et$_2$O | |
| Temperature | 120° C. | 120° C. | 120° C. | 90° C. | 90° C. |
| Reaction Time, hrs. | 0.5 | 18 | 43 | 1.2 | 2.7 |
| Yield of C$_8$OAc, wt % | 19 | 60 | 59 | 37 | 57 |
| C$_8$H$_{17}$OAc Isomer Distribution | | | | | |
| 2- | 64% | 64% | 63% | 52% | 52% |
| 3- | 36% | 34% | 34% | 45% | 44% |
| 4- | — | 2% | 3% | 3% | 4% |

A significant improvement in selectivity to the 2-isomer is seen for the reaction over the mordenite catalyst vis-a-vis the conventional BF$_3$-Et$_2$O carboxylation catalyst.

EXAMPLE 5

A 1:2 molar ratio mixture of 4-octene and acetic acid was mixed with the mordenite catalyst of Example 1 and heated to reflux. Samples were taken at 4 and 22 hours and analyzed. The results are summarized in TABLE IV.

EXAMPLE 6 (Comparative)

For purposes of comparison, a mixture of 4-octene and acetic acid were heated on a steam bath to 90° C. in the presence of BF$_3$-Et$_2$O. The results of this reaction are also shown in TABLE IV.

TABLE IV

| Reaction of 4-Octene and Acetic Acid | | | | |
|---|---|---|---|---|
| | Catalyst | | | |
| | Mordenite | | BF$_3$—Et$_2$O | |
| Temperature | 120° C. | 120° C. | 90° C. | 90° C. |
| Reaction Time, hrs. | 4 | 22 | 0.6 | 4.3 |
| Yield of C$_8$OAc, wt % | 10 | 31 | 9 | 66 |
| C$_8$H$_{17}$OAc Isomer Distribution | | | | |
| 2- | 31% | 41% | 1% | 8% |
| 3- | 46% | 38% | 5% | 18% |
| 4- | 23% | 20% | 94% | 75% |

As will be seen from the data, the conventional Lewis Acid catalyst resulted in an alkyl carboxylate product which was almost entirely the 4-isomer, as would normally be expected due to the location of the carbon-carbon double bond. In contrast, the mordenite zeolite catalyst provided a product mixture having only minor amounts of the 4-isomer and a substantial increase in the proportion of the 2- and 3-isomers. The selectivity to the 2-isomer is especially surprising in view of the internal position of the unsaturated site.

Having thus described the present invention with the aid of certain specific examples thereof, it is to be understood that such examples are intended to be merely illustrative of the disclosed process. Many variations thereon may be made without departing from the spirit of the disclosed invention, as will be evident to those skilled in the art, and such variations are intended to come within the scope of the following claims.

I claim:

1. A method for the preparation of a C$_8$-alkyl carboxylate reaction product enriched in 2-octyl carboxylate, said method comprising:
    reacting a carboxylic acid compound having the formula:

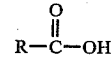

wherein R is alkyl of 1 to 10 carbon atoms with 4-octene in the presence of a dealuminized mordenite zeolite catalyst, said reaction being carried out at a temperature of between about 25° C. and 600° C. and a pressure of from about 10$^4$ Pa. to 10$^7$ Pa., to thereby produce an octyl carboxylate reaction product containing more of the 2-octyl carboxylate than of the 4-octyl carboxylate.

2. The method of claim 1 wherein said temperature is between 75° C. and 400° C.

3. The method of claim 1 wherein said pressure is between 10$^5$ Pa. and 4×10$^6$ Pa.

4. The method of claim 1 wherein said carboxylic acid compound has from 1 to about 10 carbon atoms therein.

5. The method of claim 4 wherein said carboxylic acid is acetic acid.

6. The method of claim 1, 2, 3, 4 or 5 wherein said catalyst additionally comprises a binder therefor.

* * * * *